(12) United States Patent
Winter et al.

(10) Patent No.: US 9,840,445 B2
(45) Date of Patent: Dec. 12, 2017

(54) METHOD AND APPARATUS FOR RECYCLING METHANE

(71) Applicants: John Winter, Houston, TX (US); Takahiro Obase, Houston, TX (US)

(72) Inventors: John Winter, Houston, TX (US); Takahiro Obase, Houston, TX (US)

(73) Assignee: SYNTHESIS ENERGY SYSTEMS, INC., Houston, TX (US)

( * ) Notice: Subject to any disclaimer, the term of this patent is extended or adjusted under 35 U.S.C. 154(b) by 482 days.

(21) Appl. No.: 14/210,774

(22) Filed: Mar. 14, 2014

(65) Prior Publication Data
US 2014/0298953 A1    Oct. 9, 2014

Related U.S. Application Data

(60) Provisional application No. 61/782,227, filed on Mar. 14, 2013.

(51) Int. Cl.
| | | |
|---|---|---|
| *C07C 1/00* | (2006.01) | |
| *C07C 7/12* | (2006.01) | |
| *C10J 3/48* | (2006.01) | |
| *B01J 8/18* | (2006.01) | |

(52) U.S. Cl.
CPC .............. *C07C 1/00* (2013.01); *B01J 8/1809* (2013.01); *C07C 7/12* (2013.01); *C10J 3/48* (2013.01); *B01J 2208/00274* (2013.01); *C10J 2200/152* (2013.01)

(58) Field of Classification Search
CPC .............. C10J 3/48; C07C 1/00; B01J 8/1809
See application file for complete search history.

(56) References Cited

U.S. PATENT DOCUMENTS

| | | | |
|---|---|---|---|
| 4,441,892 A * | 4/1984 | Schuster | C10J 3/54 48/197 R |
| 4,546,111 A | 10/1985 | Banquy | |
| 4,678,480 A | 7/1987 | Heinrich et al. | |
| 5,158,449 A * | 10/1992 | Bryan | F23C 10/002 110/245 |
| 2011/0189054 A1 | 8/2011 | Sheng | |
| 2011/0206594 A1 | 8/2011 | Singh et al. | |

FOREIGN PATENT DOCUMENTS

GB            1312860 A        4/1973

* cited by examiner

*Primary Examiner* — Matthew Merkling
(74) *Attorney, Agent, or Firm* — Kening Li; Miller Canfield

(57) ABSTRACT

The present invention relates to a method and gasification system for recycling methane-rich gas from syngas stream emanating from fluidized bed reactor and then returning the methane to the fluidized bed reactor. The method comprises recovering methane-rich gas from the synthesis gas and delivering at least a portion of the recovered methane-rich gas to the fluidized bed reactor. Methods to recover methane-rich gas from syngas at different steps in the gasification system are also provided herein.

9 Claims, 6 Drawing Sheets

METHOD AND APPARATUS FOR RECYCLING METHANE

CROSS-REFERENCE TO RELATED APPLICATIONS

This application claims the benefit of U.S. Provisional Application No. 61/782,227, filed Mar. 14, 2013, which is incorporated by reference herein in its entirety. Another cross-referenced U.S. Provisional Application No. 61/782,418, filed Mar. 14, 2013 is also incorporated herein by reference.

FIELD OF THE INVENTION

The present invention relates to coal gasification using fluidized bed gasifier. More specifically, the invention relates to a method and apparatus for recycling methane rich gas from syngas stream emanating from fluidized bed reactor and then returning the methane to the fluidized bed reactor.

BACKGROUND OF THE INVENTION

Fluidized bed reactors are often commonly used to gasifier carboneous materials such as coal. An example of such a gasifier is provided in U.S. patent application Ser. No. 13/532,769. A characteristic of such a gasifier is that the operating temperature of the gasifier is just below the melting point of the ash, and as such these gasifiers are called non-slagging gasifiers.

In the gasifier, solid feed stock reacts with steam and oxygen and is gasified to produce a synthesis gas ("Syngas") product containing hydrogen, carbon monoxide, carbon dioxide and methane. In addition to the partial oxidation of solid feed stock, the following reactions take place in the gasifier:

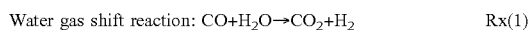

$$\text{Water gas shift reaction: } CO+H_2O \rightarrow CO_2+H_2 \quad \text{Rx(1)}$$

$$\text{Methanation (CO): } CO+3H_2 \rightarrow CH_4+H_2O \quad \text{Rx(2)}$$

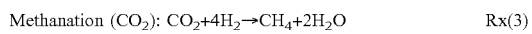

$$\text{Methanation (CO}_2\text{): } CO_2+4H_2 \rightarrow CH_4+2H_2O \quad \text{Rx(3)}$$

Syngas also comprises a significant amount of methane ($CH_4$). The amount of methane produced varies depending on reaction conditions and the composition of the feed material. For example, with coal as the feed material, and at pressures of 40 Bar and above, methane can be 15-20% of the dry syngas output. This amount of methane represents an economically significant portion of the useful syngas carbon and heating value. Yet for many applications, e.g. the use of syngas as raw material for chemical synthesis of methanol, methane is unwanted.

Currently, methane is separated and reformed to achieve economic yields of CO and $H_2$ from the original gasifier feedstock. The reforming step requires expensive equipment, and consumes significant amount of oxygen and steam. Furthermore, to maintain catalyst activity, the methane must be purified, also a very expensive step.

Therefore, there is a need in the industry for an improved process whereby methane in syngas can be converted into CO and $H_2$ without the drawbacks of the prior art processes.

SUMMARY OF THE INVENTION

Prior art attempts to recycle or reuse methane in the Syngas involve expensive steps, and the results have not been satisfactory. According to one aspect of the present invention, the methane is recycled to the fluid bed reactor to be converted to CO and $H_2$ without the use of any expensive reformer.

The present intention provides, in one aspect, a method for recycling methane for a fluidized bed coal gasifier reactor, wherein carbonaceous feed stock is fed into the fluidized bed reactor to produce synthesis gas which comprises methane, carbon monoxide and hydrogen. The method comprises recovering methane to produce a methane-rich gas from the synthesis gas and delivering at least a portion of the recovered methane-rich gas to the fluidized bed reactor.

In some embodiment of the method, the fluidized bed reactor comprises a vessel having a top and a bottom, and a conically shaped injection grid sloping downward in the vessel, wherein the grid is underneath and defining the bottom of a fluidized bed region, wherein the grid comprises a center pipe through which a fluidizing medium is provided into the fluidized bed region, and wherein a high temperature region is formed above the center pipe over the distribution grid, and at least a portion of the recovered methane-rich gas is delivered into the high temperature region.

In some embodiment of the method, the reactor comprises a vessel having a top and a bottom, and a conically shaped injection grid sloping downward in the vessel, and the grid is underneath and defining the bottom of a fluidized bed region, wherein the grid comprises a center pipe through which a fluidizing medium is provided into the fluidized bed region, and a fluidized bed of solids is formed within the vessel above the grid, the bed having a top surface, and at least a portion of the recovered methane-rich gas is delivered into the central region of the reactor below the top surface of the fluidized bed of solids.

In some embodiment of the method, at least a portion of the recovered methane-rich gas is delivered along with the carbonaceous feed stock as transport gas to assist the transport of the carbonaceous feed stock into the fluidized bed reactor.

In some embodiment of the method, fine solids particles are recovered from synthesis gas in a solids-gas separation device, and at least a portion of the recovered methane-rich gas is delivered along with the recovered solids particles as transport gas to assist the transport of the recovered solids particles into the fluidized bed reactor.

In some embodiment of the method, the synthesis gas undergoes an acid gas removal process in a gas purification apparatus, and the methane-rich gas is recovered prior to, or after, or integrated with the acid gas removal process.

In some embodiment of the method, the synthesis gas is sent to a chemical synthesis reactor where components in the synthesis gas are converted to a chemical product, and methane-rich gas is recovered from synloop gas of the chemical synthesis reactor.

In some embodiment of the method, the chemical synthesis rector comprises a methanol synthesis reactor.

In some embodiment of the method, the synthesis gas is sent to a shaft furnace where components in the synthesis gas take part in the reduction of iron ore, and methane-rich gas is recovered from effluent gas of the shaft furnace.

In some embodiment of the method, the synthesis gas is sent to an ammonia synthesis apparatus and methane-rich gas is recovered from the synthesis gas prior to the synthesis gas being introduced into the ammonia synthesis loop.

In some embodiment of the method, the method further comprises recovering methane to produce a methane-rich gas from natural gas, biogas, associated petroleum gas or a mixture thereof.

According to one aspect of the present intention, a gasification system is provided comprising (1) a fluidized bed reactor, into which carbonaceous feed stock is fed to produce synthesis gas which comprises methane, carbon monoxide and hydrogen, (2) a methane recovering apparatus for recovering a methane-rich gas from the synthesis gas, and (3) a methane delivery device for delivering at least a portion of the recovered methane-rich gas to the fluidized bed reactor.

In some embodiment of the gasification system, the reactor comprises a vessel having a top and a bottom, and a conically shaped injection grid sloping downward in the vessel, wherein the grid is underneath and defining the bottom of a fluidized bed region, wherein the grid comprises a center pipe through which a fluidizing medium is provided into the fluidized bed region, and wherein a high temperature region is formed above the center pipe over the distribution grid, and the methane delivery device delivers at least a portion of the recovered methane-rich gas into the high temperature region.

In some embodiment of the gasification system, a fluidized bed of solids is formed within the vessel above the grid, the bed having a top surface, and the methane delivery device delivers at least a portion of the recovered methane-rich gas into central region of the reactor below the top surface of the fluidized bed of solids.

In some embodiment of the gasification system, the methane delivery device delivers at least a portion of the recovered methane-rich gas along with the carbonaceous feed stock as transport gas to assist the transport of the carbonaceous feed stock into the fluidized bed reactor.

In some embodiment of the gasification system, the gasification system further comprises a solids gas separation device for recovering fine solids particles from the synthesis gas, and the methane delivery device delivers at least a portion of the recovered methane-rich gas along with the recovered solids particles as transport gas to assist the transport of the recovered solids particles into the fluidized bed reactor.

In some embodiment, the gasification system further comprises a gas purification apparatus where the synthesis gas undergoes an acid gas removal process, and the methane recovering apparatus recovers methane-rich gas prior to, or after, or integrated with the acid gas removal process.

In some embodiment of the gasification system, the gasification system of further comprises a chemical synthesis reactor where components in the synthesis gas are converted to a chemical product, and the methane recovering apparatus recovers the methane-rich gas from synloop gas (the synloop gas is defined as a effluent gas recycled to the inlet of the synthesis reactor and remained in a recycle loop) of the chemical synthesis reactor.

In some embodiment of the gasification system, the chemical synthesis rector comprises a methanol synthesis reactor.

In some embodiment of the gasification system, the gasification system further comprises a shaft furnace where components in the synthesis gas take part in the reduction of iron ore, and the methane recovering apparatus recovers the methane-rich gas from effluent gas of the shaft furnace.

In some embodiment of the gasification system, the gasification system further comprises an ammonia synthesis apparatus and the methane recovering apparatus recovers methane-rich gas prior to the synthesis gas being introduced into the ammonia synthesis apparatus.

In some embodiment of the gasification system, the methane recovering apparatus recovers methane to produce a methane-rich gas from natural gas, biogas, associated petroleum gas or from a mixture thereof.

BRIEF DESCRIPTION OF THE DRAWINGS

Embodiments according to the present invention will be further described in conjunction with accompanying figures as follows.

DESCRIPTION OF THE INVENTION

Figure 1:
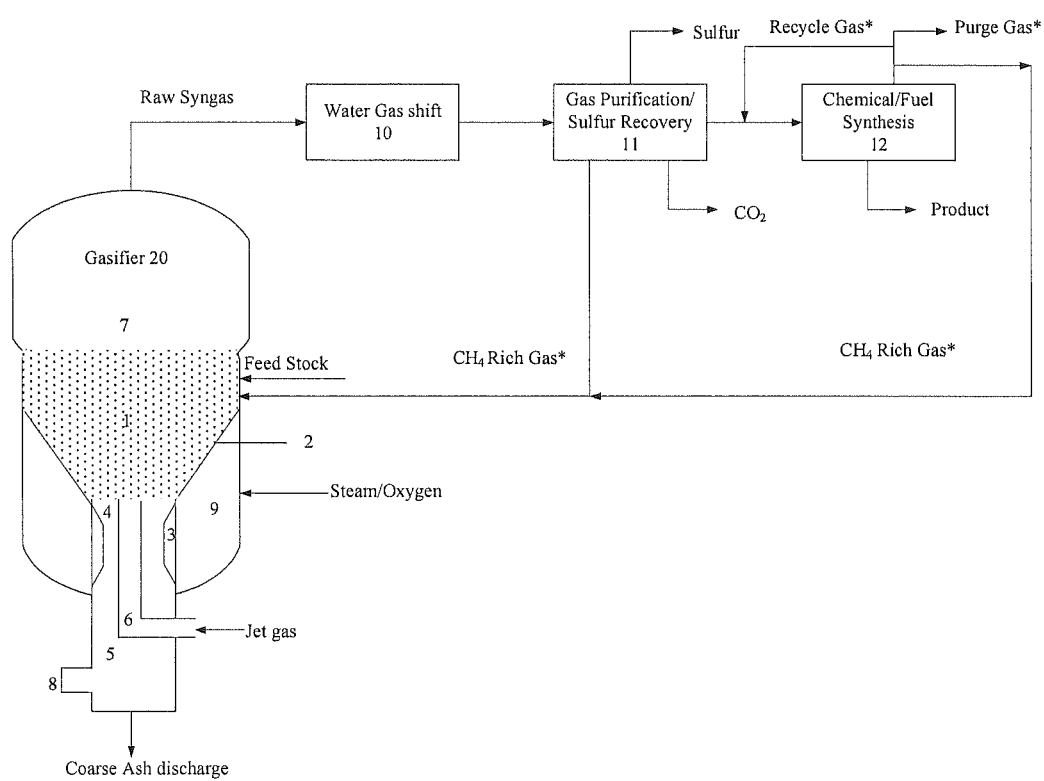
FIG. 1 schematically shows an exemplary overall arrangement of the methane recycle system according to one embodiment of the present invention.

Referring to FIG. 1, an exemplary overall arrangement of the methane recycle system according to one embodiment of the present invention is shown. A gasifier system may comprise sections as follows.

Gasifier

A fluidized bed gasifier 20 comprises vertical reaction vessel having a dense phase portion 1 and a dilute phase portion 7 above the dense phase portion, and a conical gas distribution grid 2 positioned in the reaction vessel which defines the bottom surface of the fluidized bed. A center jet pipe 6 in the center region at the bottom of the grid cone introduces oxidant to the bed. The gas stream provided through the center jet pipe 6 to the fluidized bed contains a higher oxygen concentration than oxygen concentration provided through the gas distribution grid 2. This higher oxygen concentration causes more oxidization of the feed stock in the center region of the fluidized bed, and thus the center region has a higher temperature compared to the rest of the bed. The raw syngas ascends and exits the gasifier 20 from the top, along with fine ash particles.

A fluidized bed gasifier 20 can be with or without a venturi 3 connected to the bottom of the gas distribution grid 2, with or without a classifier 5 connected to the bottom of the venturi in which classifier gas is fed through inlet 8.

The coal or other solid feed stock gasification system may be connected to a water gas shift facility 10, a gas purification/sulfur recovery system 11, and may also be linked to a chemical synthesis facility 12.

Water Gas Shift Facility

Raw syngas from the gasifier 20 can be sent to a fixed bed water gas shift reactor where water gas shift reaction as in Rx (1) takes place. Water gas shift facility 10 can be used to increase the hydrogen to carbon monoxide ratio of synthesis gas. For methanol synthesis, hydrogen to carbon monoxide ratio shall be higher than 2 stoichiometrically. To achieve this ratio, some portion of carbon monoxide in synthesis gas is converted to hydrogen by Rx (1) in a water gas shift facility.

Gas Purification/Sulfur Recovery

Most of the hydrogen sulfide and carbon dioxide are removed from the syngas by a chemical absorption process or a physical absorption process 11. Treated synthesis gas contains a few percent of carbon dioxide. The composition of the gas generally satisfies the following equation:

($H_2$ [mol %]—$CO_2$ [mol %])/(CO[mol %]+ $CO_2$ [mol %])>2.

Trace amount of sulfur compounds remaining in treated synthesis gas may be removed by adsorbent. Sulfur compounds recovered by a chemical or physical absorption process are converted to elemental sulfur, sulfuric acid, gypsum or other products by an appropriate process, well-known to those skilled in the art.

Chemical Synthesis Using Syngas as Starting Materials

Synthesis gas can be used in a variety of chemical or fuel synthesis in 12. An example of high value utilization of syngas is in methanol synthesis. Treated synthesis gas is compressed to about 100 bar and sent to a methanol synthesis reactor, where the following methanol synthesis reactions take place.

Methanol Synthesis (CO): $CO+2H_2 \rightarrow CH_3OH$   Rx (4) 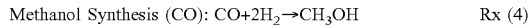

Methanol Synthesis ($CO_2$): $CO_2+3H_2 \rightarrow CH_3OH+ H_2O$   Rx (5) 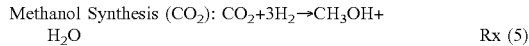

A methanol synthesis reactor is composed of a shell and tubes housed therein. Carbon monoxide, carbon dioxide and hydrogen in synthesis gas react to make methanol on the catalyst which is packed in the tubes. Methanol synthesis reactions are exothermic and the reaction heat is used to generate high pressure steam in the shell. One pass conversion of the reactor is not high because of equilibrium limitation, so unconverted synthesis gas is recycled to inlet of the methanol synthesis reactor after cooling down and separation of produced methanol and water as shown in FIG. 1. A small portion of unconverted synthesis gas was removed as purge gas to prevent accumulation of inert gas ($N_2$, Ar, $CH_4$) in the reaction loop. Another portion of the effluent gas, which is also referred as the synloop gas, is recycled to the inlet of the methanol reactor and remained in a recycle loop. In the invented flow scheme, some portion of the synloop gas can be recycled to the gasifier as transport gas.

The inventor of the present invention has discovered that in a gasifier system, the methane concentration of the syngas product is predominantly determined by temperature and pressure of the gasifier, regardless of whether there is methane introduced to the gasifier. Particularly if the methane is introduced into the central region of the gasifier well below the surface of the solids in the fluid bed, the introduced methane will have little or no effect on the methane content of the product syngas. In a SES fluid bed gasifier, there exists a distinct region of the fluid bed which is at a higher temperature as discussed above and contains a lower carbon concentration in the solids compared to the rest of the fluidized bed, even though the fluid bed is well-mixed. Therefore, gases containing methane can be introduced into this portion of the fluid bed and substantially converted to $H_2$ and CO, reducing the need to use an external methane reformer.

Accordingly, in one embodiment, for a fluidized bed reactor in which carbonaceous feed stock is fed to produce synthesis gas which comprises methane carbon monoxide and hydrogen, the present invention provides a method for recycling methane-rich gas into a gasifier. The method comprises recovering methane to produce a methane-rich gas from the synthesis gas and delivering at least a portion of the recovered methane-rich gas to the fluidized bed reactor.

Figure 2:
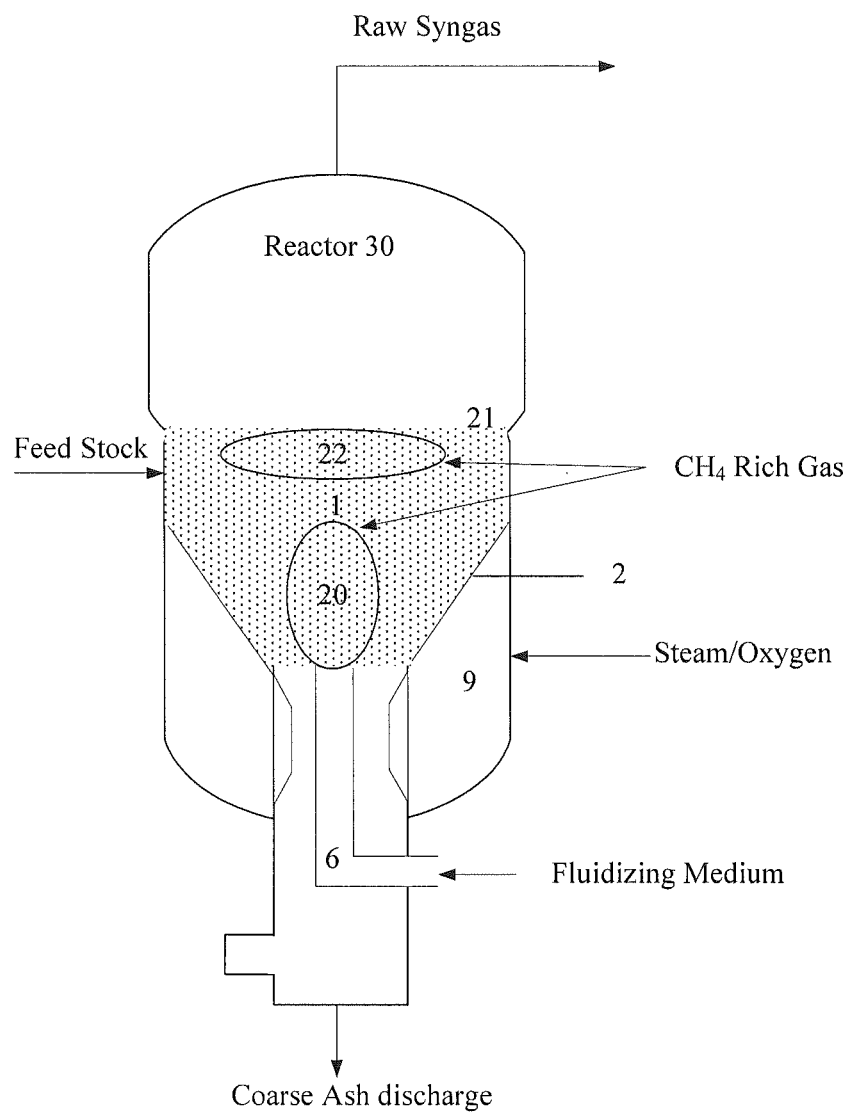
FIG. 2 shows an exemplary overall arrangement of the methane recycle system according to another embodiment of the present invention, wherein methane-rich gas is delivered to specific regions of the reactor.

Referring to FIG. 2, in one embodiment, the reactor 30 comprises a vessel having a top and a bottom and a conically shaped injection grid 2 sloping downward in the vessel. The grid 2 is underneath and defining the bottom of a fluidized bed region 1, and the grid 2 comprises a center pipe 6 through which a fluidizing medium is provided into the fluidized bed region 1. Because the fluidizing medium provided through the center jet pipe 6 contains a higher oxygen concentration than oxygen concentration provided through the grid 2, this higher oxygen concentration causes more oxidization of the feed stock in the region 20. Thus a high temperature region 20 is formed above the center pipe 6 over the distribution grid 2, and at least a portion of the methane-rich gas is delivered into the high temperature region 20.

In another embodiment, referring to FIG. 2 again, a fluidized bed 1 of solids is formed within the vessel above the grid 2, the bed having a top surface 21. At least a portion of the recovered methane-rich gas can be delivered into the central region 22 of the reactor below the top surface 21 of the fluidized bed of solids where there is a high-temperature, low-carbon region of the fluidized bed region of the gasifier.

Regardless of the above, it should be recognized that the methane-rich gas can be introduced anywhere in the dense phase 1 or even into the dilute phase region 7 with some benefit. Specific introduction of the methane-rich gas into the high temperature low carbon region offers some benefits. Firstly, since methane reforming is kinetically limited in the gasifier, introduction into the high temperature region will significantly improve the fraction reformed due to both kinetics and equilibrium, and there will not be time for the concentration to "relax" to the equilibrium amount computed at gasifier temperature. Secondly, introduction of methane will have a strong effect on the temperature of the hot center region, where there is a higher concentration of oxygen which almost immediately reacts with syngas in a highly exothermic mode, and whose amount is limited and controlled by the influx of carbon and other factors. Yet methane reformation is endothermic, reducing the temperature increase of the center region relative to the overall gasifier bed. As the gasifier limitation to keep the ash below the melting point is driven by the temperatures in this region, not the overall dense phase, controlling temperature increase in the hot center region is a key operating factor, thus confining the highly endothermic methane reforming reactions is particularly beneficial.

The methane enriched gas can be used as transport gas. In an fluidized bed gasifier system, there are various places where high pressure gas stream is used for facilitating solids flow in pneumatic transportation of the solids and the gas in these gas streams is referred to as "transport gas" or conveying gas. Conventionally, inert gas such as $CO_2$ or $N_2$ is used as transport gas, and sometimes steam or a mixture thereof is used. Transport gas is used to facilitate the delivery of coal feedstock into the gasifier, or in the delivery of ash particles recovered from the raw syngas back into the gasifier.

The normal conveying gases available to transport solids into the gasifier are nitrogen from the air separation unit, steam, or a carbon dioxide-rich stream from acid gas removal (syngas purification). The present invention uses methane-rich gas to replace other gases as transport gas, and as long as the methane-rich gas has a higher heating value than the solids transport gas it is displacing, the production of hydrogen and carbon monoxide per unit of original gasifier feedstock will increase and the consumption of oxygen per unit of hydrogen and carbon monoxide produce will decrease.

Figure 3:
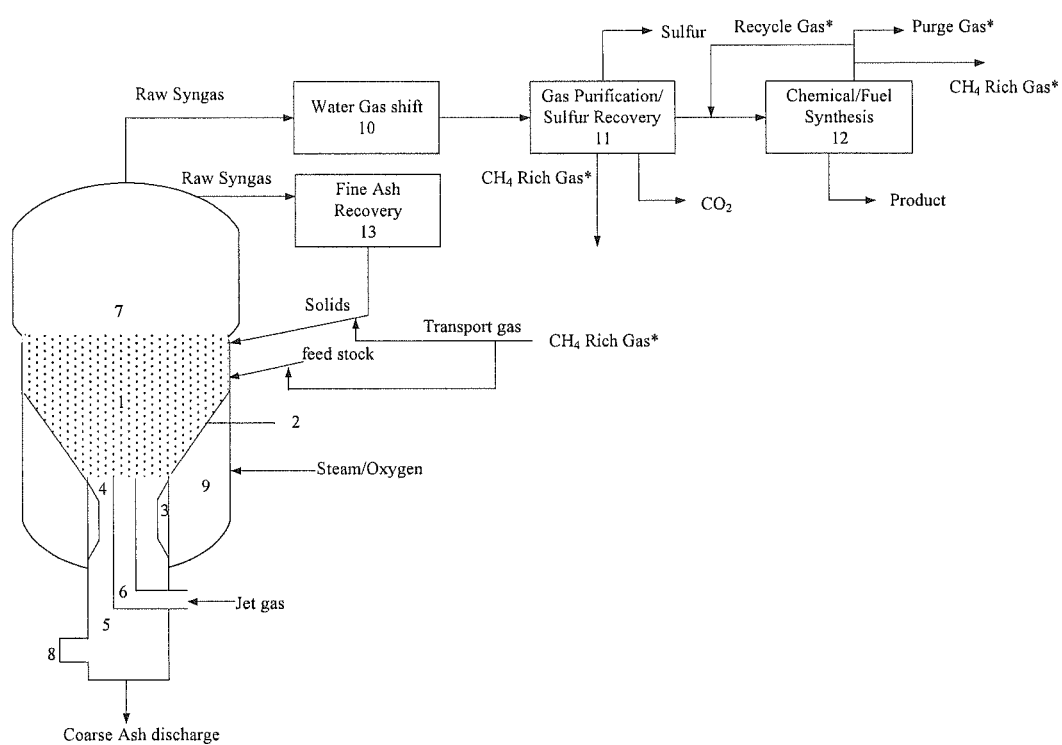
FIG. 3 shows an exemplary overall arrangement of the methane recycle system according to another embodiment of the present invention, wherein methane-rich gas is used as the transport gas.

As shown in FIG. 3, in some embodiment, at least a portion of the recovered methane-rich gas is delivered to be along with the carbonaceous feed stock (primary solids feed) to assist the transport of the carbonaceous feed stock into the fluidized bed reactor.

In some embodiment, fine solids particles are recovered from synthesis gas in a solids-gas separation device downstream of the syngas cooler (e.g. in one or more cyclones, and/or filters) as shown in FIG. 3 as fine ash recovery 13, and at least a portion of the recovered methane-rich gas is delivered along with the fine solids particles so as to assist the transport of the fine solids particles into the fluidized bed reactor.

Methane-rich gas can be recovered from the primary clean syngas at, for example, one of three places as follows:

If the gas is being shifted to produce hydrogen, for example for ammonia production, a gas containing hydrogen, carbon dioxide, and methane can be obtained. Once the carbon dioxide is removed, separation of hydrogen and methane is easily accomplished via a number of means well known in the art to those ordinarily skilled or the methane can be recovered with carbon dioxide as in the second option.

For applications where the syngas is only partially shifted or not at all, it is common to effect bulk carbon dioxide removal with a Pressure Swing Adsorption (PSA) to remove additional $CO_2$. Most methane will remain with the $CO_2$ removed in the PSA tail gas, and this gas can be used for the methane-rich stream directly, or $CO_2$ and methane can be further separated according to methods well known in the art.

In some embodiment, a gas purification apparatus is used for removing acid gas from the synthesis gas in an acid gas removal process, and the methane recovering apparatus recovers the methane-rich gas prior to, or after, or integrated with the acid gas removal process.

Other than power production, almost all processes of syngas end use generate a tail gas of unconverted CO, hydrogen and "Inert" gases. Methane in general does not react in these syngas conversion reactors (e.g. reactors for making methanol, ammonia, diesel, ethanol, gasoline, acetic acid or other chemicals) and will remain with the true inert gases in the tail gases from the syngas conversion reactor. A significant fraction of these gases can be used as the methane-rich gas. Therefore, when syngas is converted to any of commercial chemicals, methane-rich gas can be recovered from the tail gas.

As a specific example, in one embodiment, product syngas containing methane is used for the production of methanol, whereby CO, $CO_2$ and $H_2$ in syngas are fed to a methanol synthesis reactor, and are converted to methanol, while $CH_4$ passes through the reactor without being converted. Because methanol and water are condensed in the reactor's effluent gas cooling section and separated form the gas, while $CH_4$ remains in the gas, the $CH_4$ concentration in the effluent gas is higher than in the feed syngas.

In addition, most of the effluent gas is recycled to the inlet of the reactor, resulting in further accumulation of methane in the recycle loop (called synloop). The synloop gas is defined as a effluent gas recycled to the inlet of the synthesis reactor and remained in a recycle loop. This synloop gas can be recycled to the gasifier according to the present invention.

In another embodiment, syngas is used for the production of direct reduced iron (DRI) in a shaft furnace, whereby syngas and iron ore are fed to the equipment and reduction of iron ore by CO and $H_2$ in syngas takes place. Because $CH_4$ does not take part in this reaction, it is enriched in the effluent gas ("shaft furnace gas"). The shaft furnace gas from the shaft furnace is recycled to the gasifier according to the present invention.

In some embodiment, the synthesis gas is sent to ammonia synthesis apparatus and the methane-rich gas is recovered from the synthesis gas prior to the synthesis gas being introduced into the ammonia synthesis loop.

It should be noted that methane does not need to be recovered in a pure form, but from a practical standpoint the methane recovery should exceed about 50% of the methane contained in the syngas product.

The present invention is based on the insight that methane is more efficiently converted if it is delivered to the bottom central portion of the gasifier where temperatures are higher than the rest of the fluid bed. Additionally, it has been discovered that to the extent that the methane-containing recycle gas is used to displace gas that would otherwise be used to convey recycled fines or the principal solid feedstock to the gasifier, overall gasifier efficiency will be improved. Further, the present invention provides several methods to recycle the methane-rich gas from the syngas.

The example below illustrates the results for production of ammonia from a low quality coal using an SES gasifier and standard ammonia synthesis technology, comparing one example flow of the present invention with two conventional flows.

Figure 4:
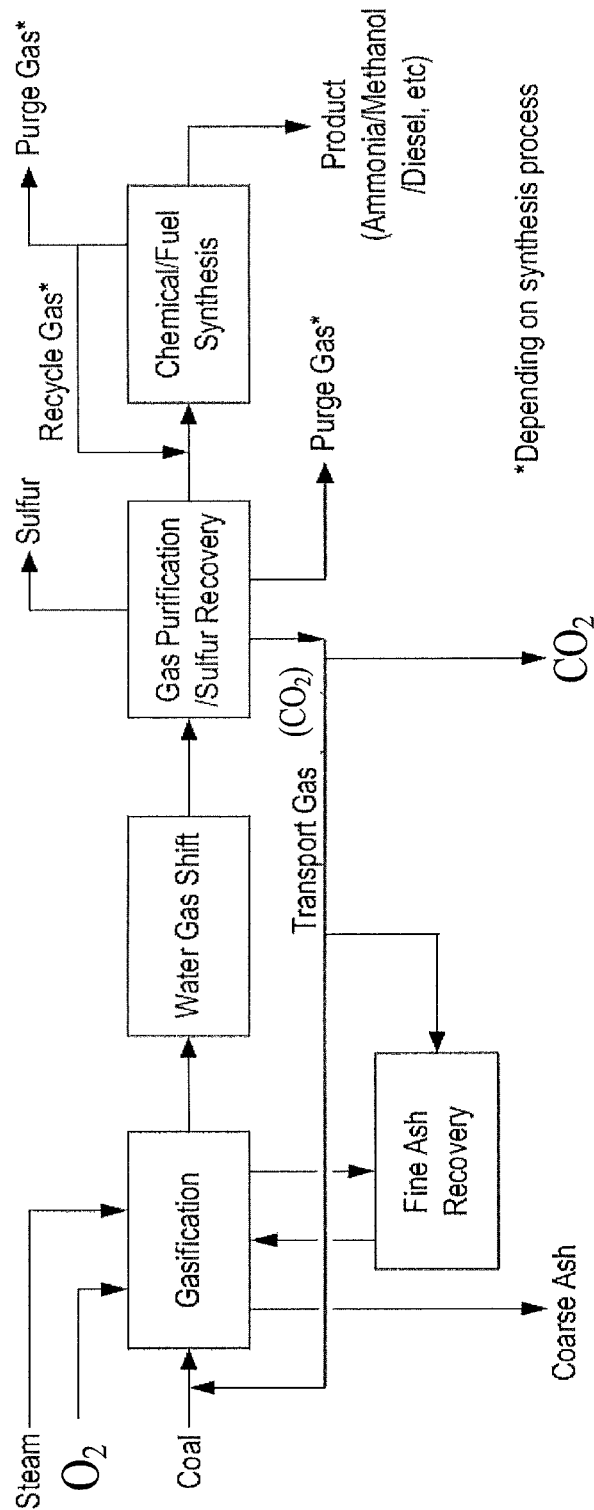
FIG. 4 is a block flow diagram of the conventional method wherein $CO_2$ is used as the transport gas.

FIG. 4 illustrates a block flow diagram of the conventional method using carbon dioxide ($CO_2$) as the transport gas. Carbon dioxide recovered from syngas purification section and used as the transport gas is the normal practice with Synthesis Energy Systems or other gasifiers in the art. (case 1)

Figure 5:
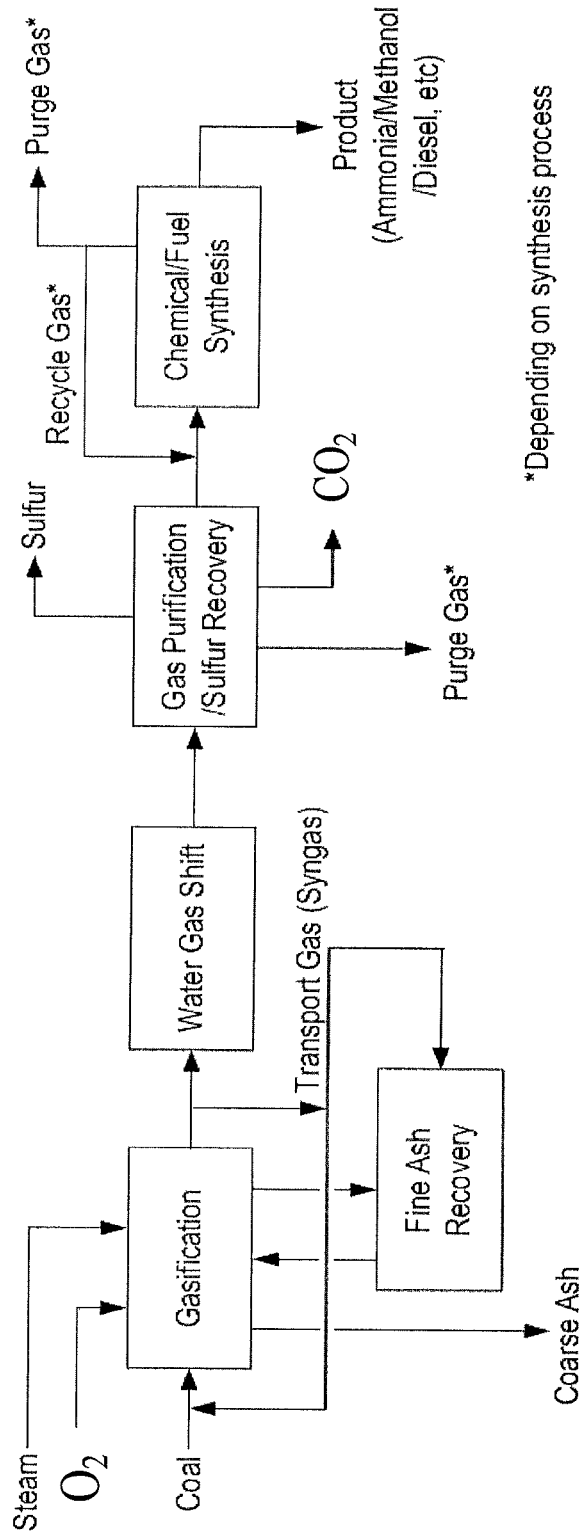
FIG. 5 is a block flow diagram of the conventional method wherein Syngas is used as the transport gas.

FIG. 5 illustrates a block flow diagram of the conventional method using raw syngas as the transport gas. (case 2)

Figure 6:
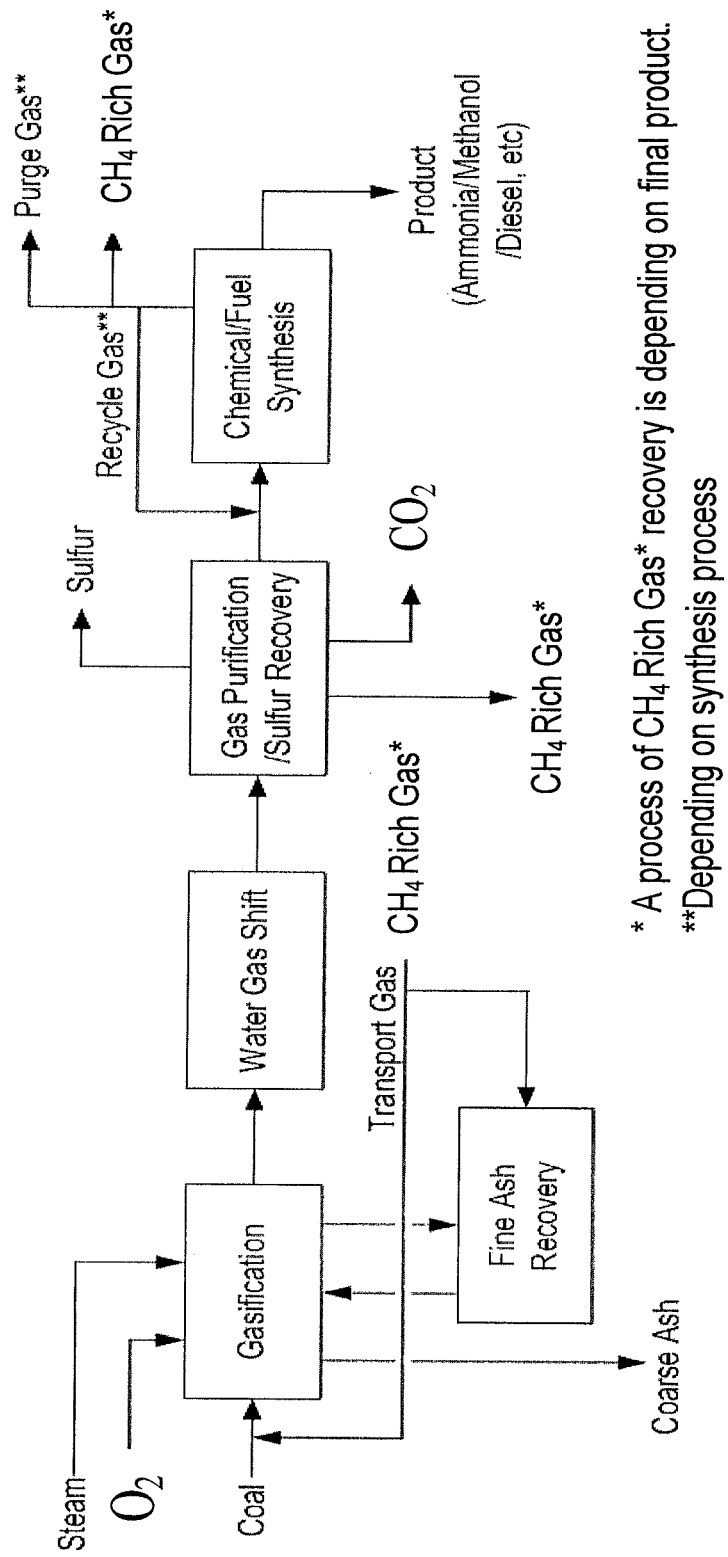
FIG. 6 is a block flow diagram of one embodiment according to the present invention wherein methane-enriched gas is recycled and used as the transport gas.

FIG. 6 illustrates a block flow diagram of an embodiment of the present invention wherein recovered methane-rich gas is used as the transport gas. The methane-rich purge gas is recovered from a PSA unit in the acid gas purification section. (case 3)

A comparison of the specific oxygen, coal and power consumption for these three cases is shown in Table 1. Further, based on Case 1, the percent decrease of oxygen, coal and power consumption according to the embodiment of Case 3 are shown in Table 2.

TABLE 1

|  | Specific $O_2$ consumption $O_2$ (kg/h) | Specific Coal consumption Coal(kg/h) | Specific Power consumption Power(kW) |
| --- | --- | --- | --- |
| Case1 | 1.50 | 3.66 | 1.17 |
| Case2 | 1.52 | 3.77 | 1.16 |
| Case3 | 1.44 | 3.53 | 1.15 |

TABLE 2

|  | Specific $O_2$ consumption | Specific Coal consumption | Specific Power consumption |
| --- | --- | --- | --- |
| Case1 | Base | Base | Base |
| Case2 | 101% | 103% | 99% |
| Case3 | 96% | 96% | 98-99% |

The use of systems according to the present invention can achieve improved yields of $H_2$ and CO per unit feedstock for solids gasification in high pressure (>5 bar) fluid bed gasification without the expenses for a separate methane reforming step and associated capital expenditure. Because methane represents 3-4 moles of the desired hydrogen, depending on the efficiency of the reforming step, in a typical dry syngas containing 10-15% methane, the methane can represent half or more of the available syngas per unit of original gasifier feedstock. In addition, for applications such as ammonia synthesis, where hydrogen is the desired product, removal and recycle of the methane prior to the chemical synthesis loop significantly enhances the efficiency and yield of the chemical synthesis loop.

Moreover, the gasification system and method provided according to the present invention can also be used to recover methane to produce a methane-rich gas from various methane containing gas, for example, natural gas, biogas, associated petroleum gas, or a mixture thereof. Thus, methane in these gases can be introduced into a fluid bed and substantially converted to $H_2$ and CO, without the need to use an external methane reformer.

It is understood that examples and embodiments described herein are for illustrative purpose only and that various modifications or changes in light thereof will be suggested to persons skilled in the art and are to be included within the spirit and purview of this application and scope of the appended claims. As discussed above, methane-rich gas can be recycled at different steps of the invented flow. Different embodiments may comprise different process units or reactors, and those skilled in the art upon review of the disclosure.

All publications, patents and patent applications cited in this patent are hereby incorporated by reference for all purposes.

One or more features from any embodiment maybe combined with one or more features of any other embodiment without departing from the scope of the disclosure. The above description is illustrative and is not restrictive. Many variations of the invention will become apparent to those skilled in the art upon review of the disclosure. The scope of the invention should, therefore, be determined not with reference to the above description, but instead should be determined with reference to the claims along with their full scope or equivalents.

What is claimed is:

1. A gasification system comprising:
    a fluidized bed reactor into which carbonaceous feed stock is fed to produce synthesis gas which comprises methane, carbon monoxide and hydrogen, wherein the fluidized bed reactor comprises a vessel having a top and a bottom, and a conically shaped injection grid sloping downward in the vessel, wherein the grid is underneath and defining the bottom of a fluidized bed region, wherein the grid comprises a center pipe through which a fluidizing medium is provided into the fluidized bed region, and wherein a high temperature region is formed above the center pipe over the distribution grid,
    a methane recovering apparatus for recovering methane to produce a methane-rich gas from the synthesis gas, and
    a methane delivery device for delivering at least a portion of the recovered methane-rich gas to the fluidized bed reactor, wherein the methane delivery device delivers at least a portion of the methane-rich gas into the high temperature region,
    wherein the gasification system further comprises a chemical synthesis reactor where components in the synthesis gas are converted to a chemical product, and wherein the methane recovering apparatus recovers methane-rich gas from synloop gas of the chemical synthesis reactor.

2. The gasification system of claim 1, wherein the reactor comprises a vessel having a top and a bottom, and a conically shaped injection grid sloping downward in the vessel, wherein the grid is underneath and defining the bottom of a fluidized bed region, wherein the grid comprises a center pipe through which a fluidizing medium is provided into the fluidized bed region, and wherein a fluidized bed of solids is formed within the vessel above the grid, the bed having a top surface, and wherein the methane delivery device delivers at least a portion of the methane-rich gas into central region of the reactor below the top surface of the fluidized bed of solids.

3. The gasification system of claim 1, wherein the methane delivery device delivers at least a portion of the recovered methane-rich gas along with the carbonaceous feed stock as transport gas to assist the transport of the carbonaceous feed stock into the fluidized bed reactor.

4. The gasification system of claim 1, further comprising solids gas separation device for recovering fine solids particles from the synthesis gas, and
    wherein the methane delivery device delivers at least a portion of the methane-rich gas along with the recovered solids particles as transport gas to assist the transport of the recovered solids particles into the fluidized bed reactor.

5. The gasification system of claim 1, further comprising a gas purification apparatus where the synthesis gas undergoes an acid gas removal process, and
    wherein the methane recovering apparatus recovers the methane-rich gas prior to, or after, or integrated with the acid gas removal process.

6. The gasification system of claim 1, wherein the chemical synthesis rector comprises a methanol synthesis reactor.

7. The gasification system according to claim 1, further comprising
    a shaft furnace where components in the synthesis gas take part in the reduction of iron ore, and
    wherein the methane recovering apparatus recovers methane-rich gas from effluent gas of the shaft furnace.

8. The gasification system according to claim 1, further comprising
    an ammonia synthesis apparatus, and
    wherein the methane recovering apparatus recovers methane-rich gas prior to the synthesis gas being introduced into the ammonia synthesis apparatus.

9. The gasification system according to claim 1, wherein the methane recovering apparatus recovers methane to produce a methane-rich gas from natural gas, biogas, associated petroleum gas or from a mixture thereof.

* * * * *